United States Patent [19]

Bennett

[11] Patent Number: Plant 5,637

[45] Date of Patent: Jan. 21, 1986

[54] MINIATURE ROSE PLANT-JEAN KENNEALLY

[76] Inventor: Cecilia L. D. Bennett, 489 Minot Ave., Chula Vista, Calif. 92010

[21] Appl. No.: 617,991

[22] Filed: Jun. 6, 1984

[51] Int. Cl.[4] ..... A01H 5/00

[52] U.S. Cl. ..... Plt./9

[58] Field of Search ..... Plt./7, 9

*Primary Examiner*—Robert E. Bagwill

[57] ABSTRACT

The subject of the present disclosure is a new and distinct variety of miniature rose plant, named 'Jean Kenneally', which is characterized by its rich Apricot colored blooms with deeper tones of Mars Orange on the under side of the central petals and hybrid tea-type form. It has a vigorous growth habit.

1 Drawing Figure

1

The present invention relates to a new and distinct variety of a hardy, dwarf, bush plant of the miniature class; the variety being primarily characterized as an apricot blend.

The variety is further characterized by:

Long stemmed blooms of hybrid tea-type form, borne usually one to a stem but on occasion in sprays of 3 to 5 or more. The blooms are held very erect and well above the foliage.

It has a slight fragrance.

The plant ranges in height from 15 to 24 inches (4 to 6 cm). The canes are sturdy and erect with moderate branching and medium to heavy foliage covering. The plant is a moderate to heavy bloomer that does well either in the green house or outdoors.

The plant has good growth habits, well shaped and attractive, bearing numerous leaflets of average size.

The seed parent was Futura (U.S. Plant Pat. No. 3,569), and the pollen parent was Party Girl (U.S. Plant Pat. No. 4,598). It differs from its seed parent in the following ways. It is a miniature with apricot coloring rather than a hybrid tea of the orange-red class. It differs from the pollen parent in the following ways. It has a distinctly apricot color from bud to fully opened bloom. The small area of near Barium Yellow at the base of each petal fades rapidly as the blooms opens and is not visible unless the petals are removed from the flower. Whereas its pollen parent, Party Girl, is a yellow blend that has visible yellow over most of the petal surfaces that becomes more apparent as the bloom matures. Party Girl will occasionally produce blooms with shadings of pink, whereas Jean Kenneally never varies from apricot tones as the bloom matures.

The descriptive matter which follows pertains to roses grown and color values observed in plants and newly opened blooms in the months of August 1983 through May 1984. The plants were grown outdoors in Chula Vista, Calif., and are believed to be accurate standards for this cultivar in similar conditions of soil and climate elsewhere.

The color photograph illustrates the variety.

Referring now specifically to the new and distinct variety of miniature rose plant named 'Jean Kenneally', the following is a detailed description thereof in outline; all major color plate identifications being by reference to The British Colour Council Horticultural Colour Chart, except where common terms of color definition are employed.

2

Type: Hardy, dwarf, bushy, green house or outdoor, exhibition quality or garden decorative potted plant.

Class: Miniature.

Variety name: Jean Kenneally.

Flowers borne: Usually one to a stem, but occasionally in sprays of 3 to 5 or more on erect stems with foliage well below the blooms.

Quantity of bloom: Moderate to heavy both outdoors or green house grown.

Bud:

*Peduncle.*—Average length (20 to 30 mm); average diameter and sturdy; near Lettuce Green (861/1 to 86/1 page 176) with light to heavy tinting of bronze.

*Hairs.*—Extremely small and numerous; located over the entire surface of the peduncle and sepals, but not present on the calyx tube.

*Calyx.*—Color near Lettuce Green (861/2 to 861/3 page 176).

*Opening.*—Opens well in all weather.

Bloom:

*Size when fully open.*—Average for a miniature variety (35 to 45 mm).

*Petalage.*—Double — Averaging about 20 to 25 petals, arranged regularly, plus petaloids (3 to 5 or more).

*Form.*—Urn-shapd to ovoid as the bloom progresses. The petals remain at first somewhat tightly cupped with the tips and/or margins reflexed outward, becoming at maturity more loosely cupped; and the petals reflex more tightly (quilling), until each row of petals forms a five pointed star.

Petals: Fairly thick with good substance; both the upper and under surfaces of all petals have a matte finish.

*Shape.*—Outer petals are of a very broad obovate form with a slight peak at the apex. The intermediate petals are very much like the outer petals only narrower. The inner petals are a broad lanceolate form; and the petaloids are also lanceolate form with some occasional irregularities.

Color: Newly opened flowers from plants grown outdoors (August 1983 through May 1984), Chula Vista, Calif:

*Outside petals.*—Upper surface — Ranging from near Apricot (609/2 to 609/3 page 70) to near Egyptian Buff (407/1 to 407/2 page 122) with a very small area at the base of near Barium Yellow (503 to 503/1 page 131)*.

*Under surface.*—Ranging from near Apricot (609/1 to 609/2 page 70) to near Egyptian Buff (407 to 407/1 page 122) with a very small area at the base of near Barium Yellow (503 to 503/1 page 131)*.

*Intermediate petals.*—Upper surface — Near Apricot (609/2 to 609/1 page 70) with a very small area at the base of near Barium Yellow (503 to 503/1 page 131)*.

*Under surface.*—Near Mars Orange (013/3 to 013/2 page 104) with a very small area at the base of near Barium Yellow (503 to 503/1 page 131)*.

*Inner petals.*—Upper surface — Near Apricot (609/2 to 609 page 70) with a very small area at the base of near Barium Yellow (503 to 503/1 page 131)* and slight blush on the outer margin of near Mars Orange (013/3 page 104).

*Under surface.*—Ranging from near Mars Orange (013/3 to 013/2 page 104) through near Vermilion (18/3 to 18/2 page 18) with a very small area at the base of near Barium Yellow (503 to 503/1 page 131)*.

*The small area of near Barium Yellow (503 to 503/1 page 131) that appear at the base of all the petals is only visible on petals that have been removed from the bloom. As the flowers open the near Barium Yellow fades rapidly. In fully opened flowers, it is no longer present.

*General color effect.*—Newly opened flowers — Rich Apricot with slightly darker tones on the inner petals and on the under surfaces of the petals. Three days open — Some fading of the intermediate and inner petals to shades similar to the outer petals. Five to seven days — All petals in the same colors as the outer petals with no near Barium Yellow present at the base of any petals, and some 'quilling' of the outermost petals. Spent petals drop off cleanly.

*Flower longevity.*—(April and May 1984) Plant in pot 4 to 7 days from bud with sepals down to fully opened bloom. Holding at fully opened with only slight fading of color for an additional 3 to 4 days before bloom begins to drop petals. Cut blooms at livingroom temperature 4 to 5 days or longer.

Reproductive organs:

*Stamens.*—A generous amount arranged uniformly around the pistil.

*Filaments.*—Varying in length with shorter filaments more proximal to the pistil; bright yellow color, including the anthers.

*Pollen.*—Abundant.

*Pistil.*—Long, abundant and spreading; pale yellow at the base to reddish at the top with pale yellow caps on the styles.

*Ovaries.*—All encased in calyx.

*Hips.*—Some.

*Seed.*—Few or none.

*Sepals.*—Permanent; spear-shaped; open as the bloom opens, but does not recurve against the peduncle.

Foliage:

*Leaves.*—Five to seven leaflets on the average; medium size for a miniature rose plant.

*Leaflets.*—Broad ovate-shaped.

*Marginl.*—Very serrated with occasional tinting of bronze, especially noticeable on the newer foliage.

*Color.*—Ranging from near Scheeles Green (860/3 to 860/1 page 175) with tinting of bronze on the margins of the new foliage to near Spinach Green (0960 to 0960/2 page 187) with only occasional tinting of bronze on the margins of the mature leaves. The upper surfaces have a semi-glossy finish, and the under surfaces have a matte finish of a slightly lighter shade than the upper surfaces.

*Rachis.*—Medium strength; upper surface is grooved with very small hairs over the length of it. Under surface has few if any hairs but does contain 2 to 5 small thorns.

*Stipules.*—Varying in length from small to medium; average width; tapering auricles angled outward at about 45 degrees.

Growth:

*Habit.*—Dwarf, bushy; average to tall height for a miniature rose plant.

*Growth.*—Vigorous.

*Canes.*—Medium diameter; sturdy; held very erect.

*Main stems.*—Color — Ranging from near Scheeles Green (860 to 860/2 page 175) to near Spinach Green (0960 to 0960/3 page 187) with heavy red-bronze tint on the newer stems that disappears as the stems mature.

*Thorns.*—Averaging 10 to 20 per 10 cm on the main stems and slightly fewer on the branches. Reddish in color. Small to average in size. Slender and straight.

*Branches.*—Color — Same as main stems.

The miniature rose plant and its flowers as herein described may vary in slight detail due to climate, soil and cultural conditions under which the variety may be grown; the present description being of the variety as grown at Chula Vista, Calif.

The following is claimed:

1. A new and distinct variety of miniature rose plant named 'Jean Kenneally' of hardy, dwarf, vigorous growth, attractive appearance, substantially as illustrated and described, characterized by its blooms of rich Apricot with deeper tones of Mars Orange on the under side of the central petals, this variety being easily asexually reproduced from cuttings, with flowers borne usually one to a stem, but occasionally in sprays of 3 to 5 or more.

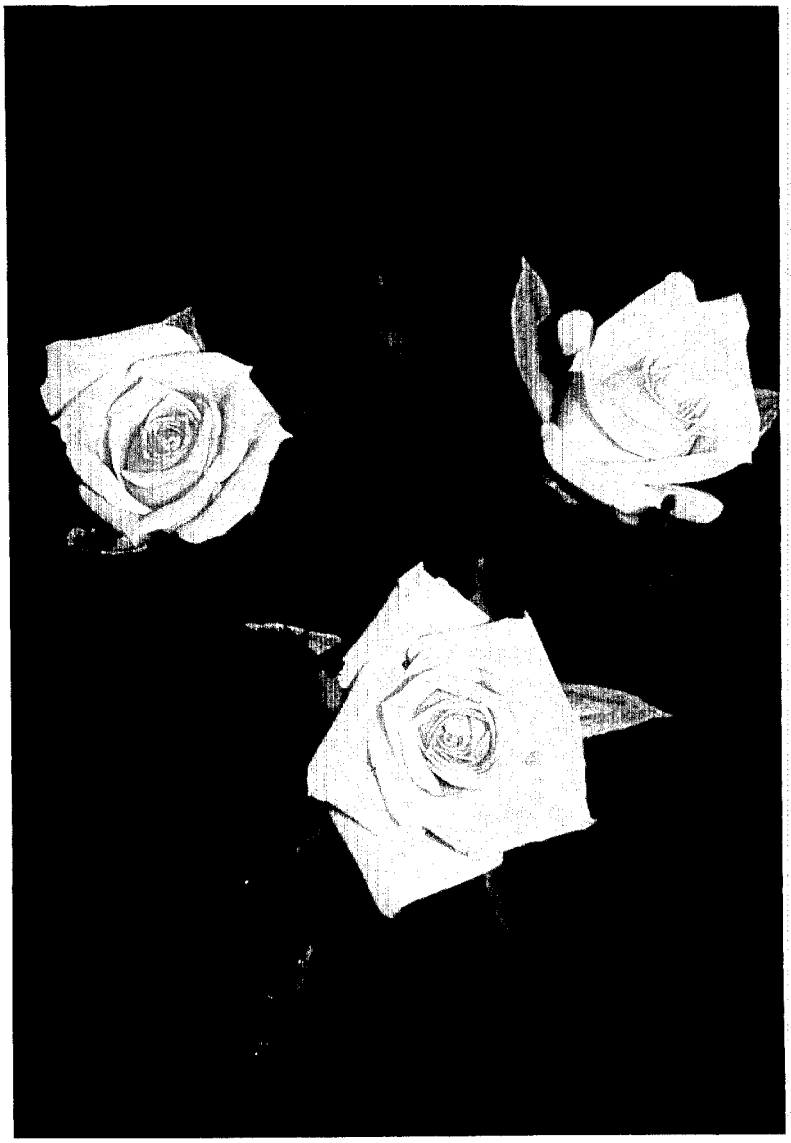

* * * * *